US010258689B2

(12) United States Patent
Choi et al.

(10) Patent No.: US 10,258,689 B2
(45) Date of Patent: Apr. 16, 2019

(54) STABLE LIQUID FORMULATION OF ETANERCEPT

(75) Inventors: Suk Young Choi, Daejeon (KR); Youn Kyung Ko, Daejeon (KR); Jin Eon So, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/123,704

(22) PCT Filed: Jun. 1, 2012

(86) PCT No.: PCT/KR2012/004369
§ 371 (c)(1),
(2), (4) Date: Jan. 15, 2014

(87) PCT Pub. No.: WO2012/165917
PCT Pub. Date: Dec. 6, 2012

(65) Prior Publication Data
US 2014/0199303 A1 Jul. 17, 2014

(30) Foreign Application Priority Data
Jun. 3, 2011 (KR) .................. 10-2011-0053890

(51) Int. Cl.
*A61K 39/395* (2006.01)
*A61K 9/00* (2006.01)
*A61K 47/18* (2017.01)
*A61K 9/08* (2006.01)
*A61K 38/17* (2006.01)
*A61K 47/20* (2006.01)

(52) U.S. Cl.
CPC ...... *A61K 39/39591* (2013.01); *A61K 9/0019* (2013.01); *A61K 9/08* (2013.01); *A61K 38/1793* (2013.01); *A61K 47/183* (2013.01); *A61K 47/20* (2013.01); *C07K 2319/30* (2013.01)

(58) Field of Classification Search
None
See application file for complete search history.

(56) References Cited

U.S. PATENT DOCUMENTS

| 5,358,708 | A | 10/1994 | Patel |
| 5,605,690 | A | 2/1997 | Jacobs et al. |
| 7,276,477 | B2 | 10/2007 | Osslund et al. |
| 7,592,004 | B2 | 9/2009 | Kaisheva et al. |
| 7,785,592 | B2 | 8/2010 | Oliver et al. |
| 2006/0292148 | A1 | 12/2006 | Matsumoto |
| 2007/0184050 | A1 | 8/2007 | Ishikawa et al. |
| 2007/0243185 | A1 | 10/2007 | Gombotz et al. |
| 2008/0160025 | A1 | 7/2008 | MacIntyre et al. |
| 2008/0286270 | A1 | 11/2008 | Oliver et al. |
| 2010/0158925 | A1 | 6/2010 | Agarkhed et al. |
| 2010/0172862 | A1* | 7/2010 | Correia ............... A61K 9/0019 424/85.2 |
| 2010/0285011 | A1 | 11/2010 | Morichika et al. |
| 2011/0020328 | A1 | 1/2011 | Brisbane et al. |
| 2011/0070231 | A1 | 3/2011 | Kaisheva et al. |
| 2014/0023649 | A1 | 1/2014 | Rao et al. |
| 2016/0090419 | A1 | 3/2016 | Morichika et al. |

FOREIGN PATENT DOCUMENTS

| CN | 1829739 A | 9/2006 |
| CN | 101426527 A | 5/2009 |
| CN | 101883588 A | 11/2010 |
| CN | 102946858 A | 2/2013 |
| EP | 1 712 240 A1 | 10/2006 |
| EP | 1 712 402 A1 | 10/2006 |
| EP | 1 478 394 B1 | 7/2008 |
| JP | 2005-527503 A | 9/2005 |
| JP | 2009-155329 A | 7/2009 |
| JP | 2009-525986 A | 7/2009 |
| JP | 2011-501671 A | 1/2011 |
| JP | 2014-519484 A | 8/2014 |
| JP | 2014-522402 A | 9/2014 |
| RU | 2380112 C2 | 1/2010 |
| WO | WO 94/06476 A1 | 3/1994 |
| WO | WO 03/072060 A2 | 9/2003 |
| WO | WO 2005/012353 A1 | 2/2005 |
| WO | WO 2005/082377 A1 | 9/2005 |

(Continued)

OTHER PUBLICATIONS

Embrel product sheet, Jan. 24, 2007, p. 1-61.*
Extended European Search Report for EP Application No. 12793393. 5, European Patent Office, The Hague, dated Oct. 29, 2014.
Office Action for Taiwanese Application No. 101119708 dated Dec. 23, 2013.
Chen, B., et al., "Influence of Histidine on the Stability and Physical Properties of a Fully Human Antibody in Aqueous and Solid Forms," *Pharmaceutical Research* 20(12):1952-1960, Plenum Publishing Corporation, United States (2003).
Ishikawa, T., et al., "Influence of pH on Heat-Induced Aggregation and Degradation of Therapeutic Monoclonal Antibodies," *Biol. Pharm. Bull.* 33(8):1413-1417, Pharmaceutical Society of Japan, Japan (Aug. 2010).

(Continued)

Primary Examiner — Yunsoo Kim
(74) Attorney, Agent, or Firm — Rothwell, Figg, Ernst & Manbeck, P.C.

(57) ABSTRACT

The present invention relates to a stable liquid formulation of etanercept (recombinant p75 sTNFR:Fc fusion protein), and more particularly, to a liquid formulation comprising one or more stabilizers selected from the group consisting of methionine, lysine, histidine, and pharmaceutically acceptable salts thereof in an amount sufficient to reduce by-product formation of etanercept during storage. The liquid formulation according to the present invention effectively reduces production of etanercept by-products and to stably maintain its pharmaceutical efficacies for long-term storage. Therefore, the reconstitution procedure is not required before administration, and the sterile formulation can be administered to patients to ensure patient safety. Thus, it can be applied to the fields in need of etanercept treatment.

3 Claims, No Drawings

(56) References Cited

FOREIGN PATENT DOCUMENTS

| WO | WO 2006/083689 A2 | 8/2006 |
|---|---|---|
| WO | WO 2007/092772 A2 | 8/2007 |
| WO | WO 2010/027364 A1 | 3/2010 |
| WO | WO 2010/106812 A1 | 9/2010 |
| WO | WO 2011/141926 A2 | 11/2011 |
| WO | WO 2011141926 A2 | 11/2011 |
| WO | WO 2012/143418 A1 | 10/2012 |
| WO | WO 2012/165917 A1 | 12/2012 |

OTHER PUBLICATIONS

Lam, X. M., et al., "Antioxidants for Prevention of Methionine Oxidation in Recombinant Monoclonal Antibody HER2," *Journal of Pharmaceutical Sciences* 86(11):1250-1255, American Chemical Society and American Pharmaceutical Association, United States (1997).

Shire, S. J., et al., "Challenges in the Development of High Protein Concentration Formulations," *Journal of Pharmaceutical Sciences* 93(6):1390-1402, Wiley-Liss, Inc. and the American Pharmacists Association, United States (2004).

Wang, W., "Instability, stabilization, and formulation of liquid protein pharmaceuticals," *International Journal of Pharmaceutics* 185:129-188, Elsevier Science B.V., Netherlands (1999).

Wang, W., et al., "Antibody Structure, Instability, and Formulation," *Journal of Pharmaceutical Sciences* 96(1):1-26, Wiley-Liss, Inc. and the American Pharmacists Association, United States (2007).

International Search Report for International Application No. PCT/KR2012/004369, Korean Intellectual Property Office, Republic of Korea, dated Oct. 29, 2012.

Office Action for Russian Patent Application No. 2013156112/10(087525), dated Sep. 22, 2014, 5 pages.

English language translation of Office Action for Russian Patent Application No. 2013156112/10(087525), dated Sep. 22, 2014, 5 pages.

First Examination Report in New Zealand Patent Application No. 618054, dated Oct. 3, 2014, 2 pages.

Further Examination Report in New Zealand Patent Application No. 618054, dated Jan. 21, 2016, 3 pages.

Office Action dated Jul. 30, 2015 in Colombian Patent Application No. 13-282255-00000-0000, with an international filing date of Jun. 1, 2012.

English Translation of Office Action dated Jul. 30, 2015 in Colombian Patent Application No. 13-282255-00000-0000, with an international filing date of Jun. 1, 2012.

Office Action dated Mar. 17, 2015 in Canadian Patent Application No. 2,837,176, with an international filing date of Jun. 1, 2012.

Office Action dated Apr. 10, 2015 in Russian Patent Application No. 2013156112/10(087525), with an international filing date of Jun. 1, 2012.

English Translation of Office Action dated Apr. 10, 2015 in Russian Patent Application No. 2013156112/10(087525), with an international filing date of Jun. 1, 2012.

* cited by examiner

STABLE LIQUID FORMULATION OF ETANERCEPT

CROSS-REFERENCE TO RELATED APPLICATIONS

This application as a U.S. national phase entry International Application No. PCT/KR2012/004369 filed Jun. 1, 2012, which claims priority to Korean Application No. KR10-2011-0053890 filed Jun. 3, 2011.

TECHNICAL FIELD

The present invention relates to a liquid formulation of etanercept (recombinant p75 sTNFR:Fc fusion protein), and more particularly, to a liquid formulation comprising one or more stabilizers selected from the group consisting of methionine, lysine, histidine, and pharmaceutically acceptable salts thereof in an amount sufficient to reduce by-products of etanercept during storage.

BACKGROUND ART

Etanercept is a biological inflammation modulator that functions as a competitive inhibitor of TNF-α, binding to cell surface TNF-α receptor, to inhibit TNF-α mediated immune responses. Etanercept is a macromolecule with a molecular weight of approximately 150 kDa, and is a homodimer of two Fc fusion proteins linked by a disulfide bond, each Fc fusion protein consisting of a human soluble p75 TNF receptor coupled to the Fc portion of human immunoglobulin G subclass 1 (Goldenberg, Clinical Therapeutics, 21(1): 75-87, 1999; Moreland et al., Ann. Intern. Med., 130(6): 478-486, 1999).

This prototypic fusion protein was first synthesized in the early 1990s by Bruce A. Beutler at the University of Texas Southwestern Medical Center, and marketed by Amgen under the trade name of Enbrel in 2002. Etanercept is a TNF-α inhibitor used to treat rheumatoid arthritis, psoriasis, and ankylosing spondylitis, and under clinical trials for the treatment of vasculitis, Alzheimer's disease, and Crohn's disease.

Like protein drugs, antibody drugs have a very short half life, and chemical and physical denaturation can be easily caused by unfavorable temperature, shear stress, vibration, freeze-thawing, UV exposure, excessive pH change, organic solvents, and microbial contamination. Chemical denaturation includes dimer dissociation, oxidation, deamidation, isomerization, and polymerization, which are influenced by the amino acids constituting the antibody and conditions of the solvent containing the antibody (salt, pH and temperature). Physical denaturation includes loss of tertiary structure, covalent/non-covalent aggregation and adhesion of monomers, which are influenced by hydrophobic patches on the protein surface changed by antibody-containing surrounding environments such as solvents, complex protein structures such as charge distribution, and thermal stability. The physical or chemical denaturation of an antibody causes loss of its physiological activities. Since the denaturation is an irreversible process, antibodies, once denatured, may not recover their native properties to the initial state, leading to a reduction in their therapeutic efficacies. It has been also suggested that aggregation of monomers causes immune responses. Therefore, many studies have been conducted on antibody formulations containing a physiologically effective amount without aggregates (Ishikawa et al., Biol. Pharm. Bull., 33(8): 1413-1417, 2010; Levin et al., The Development of Therapeutic Monoclonal Antibody Products, editors. Boston (Mass.): BioProcess Technology Consultants, Inc, Chapter 9).

There are many methods available for preventing protein denaturation in liquid formulations. In some protein drugs, the stability problems are addressed via lyophilization. For instance, U.S. Pat. No. 7,592,004 discloses a lyophilized formulation of daclizumab that is stabilized using 5 to 25 mM of a histidine buffer solution (pH 5.5 to 6.5), 0.005 to 0.03% of a non-ionic surfactant, polysorbate and 100 to 300 mM of a non-reducing sugar, sucrose. U.S. Patent Publication No. 2010-0158925 discloses a lyophilized formulation of cetuximab that is stabilized using a histidine buffer solution and lactobionic acid. However, the lyophilization process generates freezing and drying stresses such as formation of ice crystals, pH change, and high concentration of solute, and these stresses may cause antibody denaturation. In addition, since a large-capacity lyophilizer is needed for the lyophilization process during the production, high production costs arise during a large scale of production. Dissolving the lyophilized product in sterile aqueous media for reconstitution before use also poses an inconvenience.

As an alternative to solve these limitations, a stabilizer is added in liquid formulations for the improvement of antibody stability. Surfactants, serum albumins, polysaccharides, amino acids, polymers, salts or the like are known as stabilizers for proteins including antibodies (Wang, Int. J. Pharm., 185: 129-188, 1999; Wang et al., J. Pharm. Sci., 96(1): 1-26, 2007).

US Patent Publication No. 2011-0070231 discloses a stable liquid composition of IgG antibody, in which the stable pharmaceutical liquid formulation includes 50 mg/mL or more of daclizumab in 20 to 60 mM of a succinate buffet solution (pH 5.5 to 6.5), 0.02 to 0.04% of polysorbate, and 75 to 150 mM of sodium chloride.

US Patent Publication No. 2011-0020328 discloses a therapeutically effective amount of anti-CD20 antibody formulation, in which the pharmaceutically stable composition includes 10 to 100 mM of sodium acetate, 25 to 100 mM of sodium chloride, 0.5 to 5% of arginine free base, 0.02 to 0.2 mM of EDTA and 0.01 to 0.2% of polysorbate 80, and its pH is 5.0 to 7.0.

U.S. Pat. No. 7,785,592 discloses a stable formulation, in which 75 mg/mL or more of palivizumab is stabilized by using a histidine buffer solution and glycine without ionic salts and a surfactant, and its stability is maintained at 2 to 8° C. for at least 15 months.

U.S. Pat. No. 6,991,790 discloses a stable aqueous pharmaceutical formulation, including a therapeutically effective amount of an antibody, an acetate buffer solution of approximately pH 4.8 to 5.5, a surfactant, and a polyol without an isotonic agent such as sodium chloride.

U.S. Pat. No. 7,648,702 discloses a liquid formulation, in which a fusion protein of the human p75 tumor necrosis factor receptor linked to the Fc portion of the human immunoglobulin G1 (IgG1) is stabilized by using approximately 10 to 200 mM of L-arginine as an aggregation preventing agent. This patent is the only technique of using etanercept as an active ingredient.

In order to prepare stable formulations, however, appropriate stabilizers should be used considering the physicochemical properties of each active ingredient. When the stabilizers are used in combination, competition therebetween and adverse effects may lead to undesirable effects. In addition, the concentrations of antibodies should be within the range suitable for the stabilization, and their concentrations are relatively higher than those of protein drugs. Thus, much effort and caution are required to stabilize antibodies in solutions (Shire et al., J. Pharm. Sci., 93(6): 1390-1402, 2004).

There are few studies on the stable liquid formulations of etanercept, and the only method for stabilizing etanercept that the inventors are aware of is to use L-arginine in the liquid formulation. Therefore, there is an urgent need to develop a new liquid formulation which is able to stably maintain the activity of etanercept for a long period and which is more effective in etancercept stabilization than the known formulation comprising L-arginine.

DISCLOSURE

Technical Problem

The present inventors have made many efforts to develop a method for preparing a liquid formulation capable of stably maintaining the activity of etanercept. As a result, they found that one or more stabilizers selected from the group consisting of methionine, lysine, and histidine show remarkable effects on the stabilization of etanercept in a solution, thereby completing the present invention.

Technical Solution

An object of the present invention is to provide an aqueous formulation, comprising stabilizers for reducing formation of etanercept by-products during storage in a solution and maintaining its activity for a long period of time.

Advantageous Effects

The liquid formulation according to the present invention can effectively prevent formation of etanercept by-products and stably maintain its pharmaceutical efficacies for long-term storage. Therefore, the reconstitution procedure is not required before administration, and the sterile formulation can be administered to patients to ensure patient safety. Thus, it is expected to be applied to the fields in need of etanercept treatment.

BEST MODE

In one aspect to achieve the above object, the present invention provides a liquid formulation, comprising one or more stabilizers selected from the group consisting of methionine, lysine, histidine, and pharmaceutically acceptable salts thereof.

The formulation of the present invention may be a liquid formulation of etanercept comprising, etanercept; and one or more stabilizers selected from the group consisting of methionine, lysine, histidine, and pharmaceutically acceptable salts thereof.

The formulation shows increased storage stability by reducing etanercept by-products that are produced due to denaturation during storage.

As a stabilizer, methionine, lysine, histidine, or pharmaceutically acceptable salts thereof may be present in the formulation in an amount of 0.1 to 250 mM.

Etanercept in the formulation may be present in an amount of 1 to 100 mg/mL.

The formulation may further include one or more materials selected from the group consisting of a buffer, an isotonic agent, an excipient, and a preservative.

The buffer may be selected from the group consisting of citrate, phosphate, succinate, tartrate, fumarate, gluconate, oxalate, lactate, acetate, histidine, and Tris, and may be present in an amount of 0.1 to 100 mM.

The isotonic agent may be selected from the group consisting of sodium chloride, potassium chloride, boric acid, sodium borate, mannitol, glycerin, propylene glycol, polyethylene glycol, maltose, sucrose, erythritol, arabitol, xylitol, sorbitol, and glucose, and may be present in an amount of 1 to 1000 mM.

The formulation of etanercept according to the present invention may be a liquid formulation, comprising 1 to 100 mg/mL of etanercept, 0.1 to 250 mM of methionine or pharmaceutically acceptable salts thereof, 0.1 to 100 mM of phosphate buffer, and 1 to 1000 mM of sodium chloride.

The formulation of etanercept according to the present invention may be a liquid formulation, comprising 1 to 100 mg/mL of etanercept, 0.1 to 250 mM of lysine or pharmaceutically acceptable salts thereof, 0.1 to 100 mM of phosphate buffer, and 1 to 1000 mM of sodium chloride.

The formulation of etanercept according to the present invention may be a liquid formulation, comprising 1 to 100 mg/mL of etanercept, 0.1 to 250 mM of histidine or pharmaceutically acceptable salts thereof, 0.1 to 100 mM of phosphate buffer, and 1 to 1000 mM of sodium chloride.

The formulation of etanercept according to the present invention may be a liquid formulation, comprising 1 to 100 mg/mL of etanercept, 0.1 to 250 mM of histidine or pharmaceutically acceptable salts thereof, 0.1 to 250 mM of lysine or pharmaceutically acceptable salts thereof, 0.1 to 100 mM of phosphate buffer, and 1 to 1000 mM of sodium chloride.

The formulation of etanercept according to the present invention may be a liquid formulation, comprising 1 to 100 mg/mL of etanercept, 0.1 to 250 mM of histidine or pharmaceutically acceptable salts thereof, 0.1 to 250 mM of methionine or pharmaceutically acceptable salts thereof, 0.1 to 100 mM of phosphate buffer, and 1 to 1000 mM of sodium chloride.

The formulation of etanercept according to the present invention may be a liquid formulation, comprising 1 to 100 mg/mL of etanercept, 0.1 to 250 mM of methionine or pharmaceutically acceptable salts thereof, 0.1 to 250 mM of lysine or pharmaceutically acceptable salts thereof, 0.1 to 100 mM of phosphate buffer, and 1 to 1000 mM of sodium chloride.

DETAIL

The present invention has demonstrated for the first time that methionine, lysine, histidine and pharmaceutically acceptable salts thereof have the effects of reducing formation of etanercept by-products in solution and stably maintaining its activity for long-term storage, and thus suggests a novel use thereof as stabilizers of a pharmaceutically effective amount of etanercept.

In order to prepare stable formulations, appropriate stabilizers should be used considering the physicochemical properties of each active ingredient. According to the difference in types, concentration, and combinations of materials included in a formulation, competition between the materials in the formulation can lead to undesirable effects. Thus, it is difficult to prepare a stable drug specific formulation.

In the light of the above background, the present inventors have found that the liquid formulation comprising one or more stabilizers selected from the group consisting of methionine, lysine, and histidine, and pharmaceutically acceptable salts thereof increases storage stability of etanercept compared to the formulation having no stabilizers, by reducing etanercept by-products during storage in a solution.

Specifically, in one embodiment of the present invention, in order to investigate the optimal stabilizer for the preparation of the stable liquid formulation of etanercept, a variety of amino acids, surfactants, and polymers are added to examine their stabilization effects. As a result, lysine, histidine, methionine, or the combination thereof was found to show remarkable effects on stabilizing etanercept by preventing its denaturation during storage in a solution at high temperature.

Further, the formulation according to the present invention was found to show etanercept stabilizing effects which were equivalent to or higher than that of the formulation comprising L-arginine which is the known stable formulation of etanercept (U.S. Pat. No. 7,648,702). In particular, methionine was found to show the very excellent effect of stabilizing etanercept better than L-arginine.

Specifically, etanercept by-products formed during storage were examined by Size Exclusion-HPLC (SE-HPLC). As a result, compared to the total amount of impurities of the etanercept formulation that was prepared by using L-arginine as the stabilizer in U.S. Pat. No. 7,648,702, the formulation prepared using lysine as the stabilizer showed a similar amount of impurities, and the formulation prepared using histidine or methionine as the stabilizer showed a lower amount of impurities (see Table 2). Hydrophobic Interaction-HPLC (HI-HPLC) analysis also showed similar results. These results indicate that histidine, lysine, and methionine prevent etanercept denaturation to inhibit formation of by-products thereof (see Table 3).

Therefore, the liquid formulation according to the present invention can stably maintain pharmaceutical efficacies of etanercept for a long period of time by effectively reducing formation of etanercept by-products.

As used herein, the term "etanercept (recombinant p75 sTNFR:Fc fusion protein)" refers to a protein which is a homodimer form of two Fc fusion proteins linked by disulfide bonds, each Fc fusion protein consisting of a human soluble 75 kilodalton (p75) TNF (tumor necrosis factor) receptor coupled to the Fc portion of human IgG1.

Specifically, etanercept is a homodimer form of two Fc fusion proteins linked by 3 disulfide bonds, each Fc fusion protein consisting of the extracellular ligand-binding portion of the human soluble p75 TNF receptor linked to the Fc portion of human IgG1. The Fc component of etanercept contains the CH2 domain, the CH3 domain and hinge region, but not the CH1 domain of IgG1. The etanercept may have a molecular weight of approximately 150 kilodaltons (kDa). This etanercept may be currently sold under the trade name ENBREL® (Amgen Inc., Thousand Oaks, Calif.), and have CAS number 185243-69-0.

Etanercept may be produced by recombinant DNA technology, but is not limited thereto.

The etanercept of the present invention is a biological inflammation modulator that functions as a competitive inhibitor of TNF-α, binding to cell surface TNF-α receptor, to inhibit TNF-α mediated immune responses, and is used to treat rheumatoid arthritis, psoriasis, and ankylosing spondylitis, and is under clinical trials for the treatment of vasculitis, Alzheimer's disease, and Crohn's disease.

In the liquid formulation according to the present invention, the etanercept is contained in a therapeutically effective amount. Preferably, etanercept is present in an amount of 1 to 100 mg/ml.

As used herein, the term "stabilized liquid formulation" or "stable liquid formulation" refers to a formulation that retains the physical and chemical identity and integrity of the therapeutically active ingredient, etanercept, during storage in a solution. An analytical measurement of the etanercep stability may be performed by protein stability assay widely known in the art. The stability may be measured at a predetermined temperature for a predetermined time. For rapid assay, the formulation may be stored at a higher or "elevated" temperature, for example, 40° C. for 2 weeks to 1 month or longer, and its time-dependent stability measured at this time.

As used herein, the term "stabilizer" refers to a specific chemical that interacts with a biological molecule and/or a general pharmaceutical excipient in a formulation to improve its stability. The stabilizer generally protects proteins from air/solution interface-induced stress and solution/surface-induced stress which cause protein aggregation. In the present invention, the stabilizer is a component that reduces formation of etanercept by-products during storage in a solution to maintain its activity for a long period of time, and is preferably one or more selected from the group consisting of methionine, lysine, histidine and pharmaceutically acceptable salts thereof.

As for the amino acids, both L-forms and D-forms are included in the scope of the present invention. Not only the amino acids themselves such as methionine, lysine, and histidine, but also analogues, solvates, hydrates and stereoisomers, and the pharmaceutically acceptable salts thereof are within the scope of the present invention as long as they show substantially the same effect.

As used herein, the term "pharmaceutically acceptable salts" refers to compounds that are prepared in the form of salts of the amino acids, such as methionine, lysine, and histidine, within the range retaining their functions as the stabilizers of the present invention. Specifically, it may form a salt by acid addition, and for example, it may form a salt with an inorganic acid (e.g., hydrochloric acid, hydrobromic acid, phosphoric acid, nitric acid, sulfuric acid, etc.), organic carboxylic acid (e.g., acetic acid, halo acetic acid such as trifluoroacetic acid, propionic acid, maleic acid, succinic acid, malic acid, citric acid, tartaric acid, salicylic acid), sugar acid (glucuronic acid, galacturonic acid, gluconic acid, ascorbic acid), acidic polysaccharide (e.g., hyaluronic acid, chondroitin sulfate, arginine acid), organic sulfonic acid including sulfonic acid sugar ester such as chondroitin sulfate (e.g., methane sulfonic acid, p-toluene sulfonic acid).

As used herein, the term "analogues" refers to compounds that show the same functions as the amino acids, such as methionine, lysine, and histidine, used as stabilizers of the present invention. In the present invention, the amino acids such as methionine, lysine, and histidine include the analogues of thereof. In the present invention, examples of the analogues may include methionine analogues, namely, selenomethionine, hydroxy methyl butanoic acid, ethionine, and trifluoromethionine, but are not limited thereto.

As used herein, the term "by-products" refers to the undesirable products that reduce the ratio of the therapeutically active ingredient, etanercept, in the formulation. The typical by-products include "low molecular weight products" resulting from etanercept denaturation by deamination or hydrolysis, "high molecular weight products" such as oligomers and aggregates, or mixtures thereof.

As used herein, the term "high molecular weight products" includes etanercept fragments that are subsequently aggregated by denaturation (e.g., produced by polypeptide degradation due to deamination or hydrolysis) or mixtures thereof. Typically, the high molecular weight products are complexes having higher molecular weights than the therapeutic monomer etanercept, and may have a molecular weight of more than approximately 150 kDa.

As used herein, the term "low molecular weight products" includes, for example, therapeutic polypeptides produced by deamination or hydrolysis, namely, etanercept fragments. Typically, the low molecular weight products are complexes having lower molecular weights than the therapeutic monomer etanercept, and may have a molecular weight of less than approximately 150 kDa.

The liquid formulation of the present invention includes one or more stabilizers selected from the group consisting of methionine, lysine, histidine, and pharmaceutically acceptable salts thereof. Specifically, the liquid formulation comprises methionine, lysine, or histidine as a stabilizer, or two stabilizers such as methionine and lysine, methionine and histidine, or lysine and histidine, or three stabilizers such as methionine, lysine, and histidine. In the above formulation comprising combinations of the amino acids, the pharmaceutically acceptable salts of methionine, lysine, histidine respectively may be added further, or methionine, lysine, and histidine may be the modified forms of the pharmaceutically acceptable salts respectively. The liquid formulation comprises preferably methionine, lysine, histidine, methionine and lysine, methionine and histidine, or lysine and histidine, and more preferably methionine as a stabilizer.

Methionine is an essential amino acid, and has a chemical formula of $C_5H_{11}NO_2S$ and a molecular weight of 149.21. Methionine is a non-polar amino acid, and contains a thioether group ($—S—CH_3$) in its side chain. It has a $pK_1$ value of 2.28, $pK_2$ value of 9.21, and isoelectronic point (PI) value of 5.74. Methionine prevents oxidation of antibodies in liquid formulations to stabilize antibodies by competing with the methionine residues in antibodies for reaction with the free hydroxyl radicals (Lam et al., J. Pharm. Sci., 86(11): 1250-1255, 1997; Wang, Int. J. Pharm., 185: 129-188, 1999).

Lysine is an essential amino acid, and has a chemical formula of $C_6H_{14}N_2O_2$ and a molecular weight of 146.19. Lysine is a basic amino acid, and has a $pK_1$ value of 2.18, $pK_2$ value of 8.95, $pK_3$ value of 10.53 and PI value of 9.74.

Histidine is an essential amino acid with an imidazole functional group having positive charge in its side chain, and has a chemical formula of $C_6H_9N_3O_2$ and a molecular weight of 155.15. Histidine is a basic amino acid, and has a $pK_1$ value of 1.82, $pK_2$ value of 9.17, $pK_3$ value of 6.0 and PI value of 7.59.

In contrast, L-arginine contained in the known commercially available formulation of etanercept is an essential amino acid, and has a chemical formula of $C_6H_{14}N_4O_2$ and a molecular weight of 174.2. Arginine is a basic amino acid, and has a $pK_1$ value of 2.17, $pK_2$ value of 9.04, $pK_3$ value of 12.48 and PI value of 10.76. That is, methionine, lysine, and histidine used as a stabilizer in the present invention are totally different from arginine as a known stabilizer for etanercept in construct, chemical formula, physicochemical properties, and ionization tendency. The present invention has demonstrated for the first time that amino acids such methionine, lysine, and histidine are the appropriate stabilizers for etanercept.

The content of the stabilizer in the liquid formulation of the present invention is 0.1 to 250 mM, preferably 1 to 100 mM, and more preferably 5 to 50 mM.

The liquid formulation of the present invention may further include any material which is generally contained in formulations of protein drugs or antibody drugs to increase etanercept stability according to one or more stabilizers selected from the group consisting of methionine, lysine, histidine, and pharmaceutically acceptable salts thereof except for those deteriorating the function of the present invention. For example, L-arginine known as a stabilizer for etanercept may be added to the liquid formulation of the present invention.

The liquid formulation according to the present invention may further include a buffer in addition to the stabilizer. As used herein, the term "buffer" refers to the component that improves isotonicity and chemical stability of the formulation, and functions to maintain physiologically suitable pH. The buffer prevents a rapid pH change of the liquid formulation to maintain pH of the solution for the stabilization of etanercept. Preferred examples of the buffer include citrate, phosphate, succinate, tartrate, fumarate, gluconate, oxalate, lactate, acetate, histidine, and Tris, but are not limited thereto. In the specific embodiment, the buffer is a phosphate buffer. The buffer may be used either alone or in combinations of two or more thereof.

In the various embodiments of the present invention, the formulation should have pH of approximately 5 to 7.5 or pH of approximately 5.8 to 6.8. In the specific embodiment, the formulation has pH of approximately 6.0 to 6.6. The ranges from the intermediate to the above mentioned pH levels, for example, approximately pH 5.2 to approximately pH 6.4 (e.g., pH 6.2) are also intended to be part of this invention. For example, ranges of values using a combination of any of the above mentioned values as upper and/or lower limits are intended to be included. If necessary, the pH may be adjusted by techniques known in the art. For example, the pH may be adjusted to any desirable range by addition of HCl or by addition of histidine, if necessary.

In another embodiment, the buffer is present at a concentration of 0.1 to 100 mM, preferably 1 to 50 mM, and more preferably 5 to 25 mM. The ranges from the intermediate to the above mentioned concentrations are also intended to be part of this invention. For example, ranges of concentrations using a combination of any of the above mentioned concentrations as upper and/or lower limits are intended to be included. In the specific embodiment, the buffer should be present in an amount sufficient to maintain the physiologically sufficient pH.

The liquid formulation according to the present invention may further include an isotonic agent in addition to the stabilizer. As used herein, the term "isotonic agent" refers to a component that functions to partially maintain isotonicity of the formulation and the protein level, and partially maintain the level, ratio, or proportion of the therapeutically active polypeptide present in the formulation. The isotonic agent possesses the same osmotic pressure as blood plasma, and so can be intravenously infused into a subject without changing the osmotic pressure of the subject's blood plasma. Indeed, in one embodiment according to the present invention, isotonic agent is present in an amount sufficient to render the formulation suitable for intravenous infusion. Often, the isotonic agent serves as a bulking agent as well. As such, the isotonic agent may allow the protein to overcome various stresses such as freezing and shear.

The isotonic agent serves to maintain the proper osmotic pressure in the body, when etanercept in the solution is administered into the body. Examples of the isotonic agent may include the commonly used sodium chloride, potassium chloride, boric acid, sodium borate, mannitol, glycerin, propylene glycol, polyethylene glycol, maltose, sucrose, erythritol, arabitol, xylitol, sorbitol, and glucose, but is not limited thereto. In the specific embodiment, the isotonic agent is NaCl. These isotonic agents may be used either alone or in combinations of two or more thereof.

In still another embodiment, the isotonic agent (e.g., NaCl) is present at a concentration of 1 to 1000 mM, preferably 10 to 500 mM, and more preferably 50 to 250 mM. The ranges from the intermediate to the above mentioned concentrations are also intended to be part of this invention. For example, ranges of concentrations using a combination of any of the above mentioned concentrations as upper and/or lower limits are intended to be included. The isotonic agent should be present in an amount sufficient to maintain osmosis of the formulation.

The liquid formulation according to the present invention may further include a pharmaceutically acceptable excipient, and examples of the excipient may include sugars and polyols, surfactants, polymers or the like. Examples of the sugars and polyols may include sucrose, trehalose, lactose, maltose, galactose, mannitol, sorbitol, glycerol, examples of the surfactants may include non-ionic surfactants such as polysorbate 20, polysorbate 80, and poloxamer, and examples of the polymers may include dextran, polyethylene glycol, carboxyl methylcellulose, hyaluronic acid, and cyclodextrin.

The liquid formulation according to the present invention may further include a preservative. The preservative means a chemical that is added to pharmaceutical formulations as an antimicrobial agent. Examples of the preservative may include benzalkonium chloride, benzethonium, chlorhexidine, phenol, m-cresol, benzyl alcohol, methylparaben, propylparaben, chlorobutanol, o-cresol, p-cresol, chloro-cresol, phenylmercuric nitrate, thimerosal, and benzoic acid, but are not limited thereto. These preservatives may be used either alone or in combinations of two or more thereof.

In the specific embodiment, the formulation of the present invention is a stable liquid formulation comprising 1 to 100 mg/mL of etanercept, 0.1 to 250 mM of methionine or pharmaceutically acceptable salts thereof, 0.1 to 100 mM of phosphate buffer, and 1 to 1000 mM of sodium chloride. More specifically, the formulation of the present invention is the stable liquid formulation comprising 1 to 100 mg/mL of etanercept, 0.1 to 100 mM of methionine or pharmaceutically acceptable salts thereof, 0.1 to 50 mM of phosphate buffer, and 1 to 500 mM of sodium chloride, at pH 6.0 to 6.6.

In the specific embodiment, the formulation of the present invention is a stable liquid formulation comprising 1 to 100 mg/mL of etanercept, 0.1 to 250 mM of histidine or pharmaceutically acceptable salts thereof, 0.1 to 100 mM of phosphate buffer, and 1 to 1000 mM of sodium chloride. More specifically, the formulation of the present invention is the stable liquid formulation comprising 1 to 100 mg/mL of etanercept, 0.1 to 50 mM of histidine or pharmaceutically acceptable salts thereof, 0.1 to 50 mM of phosphate buffer, and 1 to 500 mM of sodium chloride, at pH 6.0 to 6.6.

In the specific embodiment, the formulation of the present invention is a stable liquid formulation comprising 1 to 100 mg/mL, of etanercept, 0.1 to 250 mM of lysine or pharmaceutically acceptable salts thereof, 0.1 to 100 mM of phosphate buffer, and 1 to 1000 mM of sodium chloride. More specifically, the formulation of the present invention is the stable liquid formulation comprising 1 to 100 mg/mL of etanercept, 0.1 to 100 mM of lysine or pharmaceutically acceptable salts thereof, 0.1 to 50 mM of phosphate buffer, and 1 to 500 mM of sodium chloride, at pH 6.0 to 6.6.

In the specific embodiment, the formulation of the present invention is a stable liquid formulation comprising 1 to 100 mg/mL of etanercept, 0.1 to 250 mM of histidine or pharmaceutically acceptable salts thereof, 0.1 to 250 mM of lysine or pharmaceutically acceptable salts thereof, 0.1 to 100 mM of phosphate buffer, and 1 to 1000 mM of sodium chloride. More specifically, the formulation of the present invention is the stable liquid formulation comprising 1 to 100 mg/mL of etanercept, 1 to 50 mM of histidine or pharmaceutically acceptable salts thereof, 1 to 100 mM of lysine or pharmaceutically acceptable salts thereof, 0.1 to 50 mM of phosphate buffer, and 1 to 500 mM of sodium chloride, at pH 6.0 to 6.6.

In the specific embodiment, the formulation of the present invention is a stable liquid formulation comprising 1 to 100 mg/mL of etanercept, 0.1 to 250 mM of histidine or pharmaceutically acceptable salts thereof, 0.1 to 250 mM of methionine or pharmaceutically acceptable salts thereof, 0.1 to 100 mM of phosphate buffer, and 1 to 1000 mM of sodium chloride. More specifically, the formulation of the present invention is the stable liquid formulation comprising 1 to 100 mg/mL of etanercept, 1 to 50 mM of histidine or pharmaceutically acceptable salts thereof, 1 to 100 mM of methionine or pharmaceutically acceptable salts thereof, 0.1 to 50 mM of phosphate buffer, and 1 to 500 mM of sodium chloride, at pH 6.0 to 6.6.

In the specific embodiment, the formulation of the present invention is a stable liquid formulation comprising 1 to 100 mg/mL of etanercept, 0.1 to 250 mM of methionine or pharmaceutically acceptable salts thereof, 0.1 to 250 mM of lysine or pharmaceutically acceptable salts thereof, 0.1 to 100 mM of phosphate buffer, and 1 to 1000 mM of sodium chloride. More specifically, the formulation of the present invention is the stable liquid formulation comprising 1 to 100 mg/mL of etanercept, 1 to 50 mM of methionine or pharmaceutically acceptable salts thereof, 1 to 50 mM of lysinee or pharmaceutically acceptable salts thereof, 0.1 to 50 mM of phosphate buffer, and 1 to 500 mM of sodium chloride, at pH 6.0 to 6.6.

The formulation of the present invention can be used for treatment of a disease in which etanercept is therapeutically effective. Etanercept is a biological inflammation modulator to inhibit TNF-α mediated immune responses, and the formulation of the present invention is used to treat rheumatoid arthritis, psoriasis, ankylosing spondylitis, vasculitis, Alzheimer's disease, or Crohn's disease, not limited thereto. The formulation of the present invention may be administered by oral or parenteral, i.e., subcutaneously, intramuscularly, intraperitoneail, intra-abdominal, transdermal route, and/or intravenously, but is not limited thereto.

In another aspect, the present invention provides a method for increasing stability of etanercept using a liquid formulation comprising one or more stabilizers selected from the group consisting of methionine, lysine, histidine, and pharmaceutically acceptable salts thereof.

The liquid formulation can increase storage stability of etanercept by reducing etanercept by-products that are produced due to denaturation during storage.

MODE FOR INVENTION

Hereinafter, the present invention will be described in more detail with reference to Examples. However, these Examples are for illustrative purposes only, and the invention is not intended to be limited by these Examples.

Example 1

Stability Test of Etanercept Aqueous Formulation According to Addition of Stabilizer In order to investigate the optimal stabilizer for the preparation of the stable aqueous formulation of etanercept, histidine as a stabilizer was added to a 5 mM phosphate solution to which etanercept was added to a concentration of 50 mg/mL, and sodium chloride was added thereto as an isotonic agentto prepare Formulation 1.

In addition, etanercept was added to a 10 mM phosphate solution to a concentration of 50 mg/mL, and sodium chloride was added thereto as an isotonic agent. Then, each of lysine, arginine, methionine, glycine, polysorbate 20, polysorbate 80, poloxamer 188, propylene glycol, protamine sulfate, sucrose, and guanidine HCl was added to prepare Formulations 2 to 12.

Finally, sodium chloride as the isotonic agent was added to a 10 mM phosphate solution to which etanercept was added to a concentration of 50 mg/mL to prepare a stabilizer-free formulation. The stabilizer compositions of the formulations are shown in the following Table 1. Each 0.5 mL of the prepared formulation was put in 1.0 mL glass syringes, sealed, and stored at 50° C.

TABLE 1

|  | Stabilizer composition |
|---|---|
| Formulation 1 | Histidine 10 mM |
| Formulation 2 | Lysine 25 mM |
| Formulation 3 | Arginine 25 mM |
| Formulation 4 | Methionine 25 mM |
| Formulation 5 | Glycine 1% |
| Formulation 6 | Tween 20 0.1% |
| Formulation 7 | Tween 80 0.1% |
| Formulation 8 | F68 0.1% |
| Formulation 9 | Propylene glycol 0.1% |
| Formulation 10 | Protamine sulfate 0.03% |
| Formulation 11 | Sucrose 2% |
| Formulation 12 | Guanidine HCl 0.2% |
| stabilizer-free formulation | — |

At 7 days after storage at 50° C., Formulations 1 to 12 and the stabilizer-free formulation of Table 1 were analyzed by SE-HPLC to examine the types of low molecular weight products and high molecular weight products such as oligomers and aggregates resulting from etanercept denaturation, and the total amount of these products was represented as Total Impurity. In addition, structural changes of etanercept were examined by HI-HPLC. In HI-HPLC, etanercept-related substances were separated into 4 peaks, including pre-Peak, Peak 1, Peak 2, and Peak 3. Pre-Peak and Peak 1 represent low molecular weight products, Peak 2 represents etanercept, and Peak 3 represents dimers with low aggregation or activity. Thus, the total amount of pre-Peak, Peak 1, and Peak 3 was represented as Total Impurity. The results are shown in Tables 2 and 3, respectively.

TABLE 2

|  | Total Impurity by SE-HPLC (%) | |
|---|---|---|
|  | Day 0 | Day 7 |
| Formulation 1 | 4.6 | 22.2 |
| Formulation 2 | 4.7 | 24.8 |
| Formulation 3 | 4.6 | 24.2 |
| Formulation 4 | 4.6 | 20.8 |
| Formulation 5 | 4.6 | 28.5 |
| Formulation 6 | 4.7 | 29.4 |
| Formulation 7 | 4.6 | 29.0 |
| Formulation 8 | 4.6 | 28.8 |
| Formulation 9 | 4.7 | 27.8 |
| Formulation 10 | 4.6 | 29.4 |
| Formulation 11 | 4.8 | 28.4 |

TABLE 2-continued

|  | Total Impurity by SE-HPLC (%) | |
|---|---|---|
|  | Day 0 | Day 7 |
| Formulation 12 | 4.7 | 27.5 |
| stabilizer-free formulation | 4.7 | 30.2 |

TABLE 3

|  | Total Impurity by HI-HPLC (%) | |
|---|---|---|
|  | Day 0 | Day 7 |
| Formulation 1 | 14.7 | 33.7 |
| Formulation 2 | 14.6 | 34.9 |
| Formulation 3 | 15.0 | 34.3 |
| Formulation 4 | 15.2 | 30.3 |
| Formulation 5 | 14.8 | 36.6 |
| Formulation 6 | 15.2 | 35.5 |
| Formulation 7 | 15.2 | 36.2 |
| Formulation 8 | 15.4 | 35.5 |
| Formulation 9 | 15.2 | 35.1 |
| Formulation 10 | 15.0 | 36.9 |
| Formulation 11 | 14.9 | 35.1 |
| Formulation 12 | 15.1 | 34.8 |
| stabilizer-free formulation | 14.4 | 41.9 |

As shown in the SE-HPLC results of Table 2, when stored at 50° C. for 7 days, Formulation 1 containing histidine as a stabilizer showed total impurity of 22.2%, Formulation 2 containing lysine as a stabilizer showed total impurity of 24.8%, Formulation 3 containing arginine as a stabilizer showed total impurity of 24.2%, Formulation 4 containing methionine as a stabilizer showed total impurity of 20.8%. All of them showed remarkably low Total Impurity, compared to stabilizer-free formulation showing Total Impurity of 30.2%. When these formulations were compared to Formulation 3 using L-arginine as a stabilizer (U.S. Pat. No. 7,648,702), Formulation 2 containing lysine showed similar total impurity of 24.8%, and Formulation 1 containing histidine and Formulation 4 containing methionine showed reduced Total Impurity of 22.2% and 20.8%, respectively.

The HI-HPLC results of Table 3 are similar to the SE-HPLC results. The stabilizer-free formulation showed Total Impurity of 41.9%. On the contrary, each of Formulations 1, 2, 3, and 4 showed Total Impurity of 33.7%, 34.9%, 34.3%, and 30.3% respectively, indicating that histidine, lysine, L-arginine, and methionine added in each formulation have the effects of preventing etanercept denaturation. In particular, Formulation 4 containing methionine showed the lowest Total Impurity, indicating that methionine is most effective in etanercept stabilization.

Consequently, the present invention demonstrated that lysine, histidine, and methionine have effects of stabilizing etanercept by preventing its denaturation, which are equivalent to or higher than that of L-arginine, and in particular, methionine is more effective in etanercept stabilization than L-arginine.

Example 2

Stability Test of Etanercept Aqueous Formulation According to Methionine Concentration In order to investigate the optimal concentration of methionine for the stabilization of etanercept, 120 mM sodium chloride was added to 10 mM phosphate solutions, and each of 25 mM and 12.5 mM methionine was added thereto, after which etanercept in a concentration of 50 mg/mL so was added as to prepare Formulations 13 and 14, respectively. According to the preparation of a commercially available etanercept aqueous formulation, 25 mM L-arginine was added to 100 mM sodium chloride and 1% sucrose in a 10 mM phosphate solution, and etanercept was added to a concentration of 50 mg/mL so as to prepare a control. Each 0.5 mL of the formulation was put in 1.0 mL glass syringes, sealed, and stored at 40° C., 25° C. and 4° C. The compositions of the prepared aqueous formulations are shown in the following Table 4.

TABLE 4

| | Composition |
|---|---|
| Formulation 13 | Etanercept 50 mg/mL, phosphate solution 10 mM, NaCl 120 mM, methionine 25 mM (pH 6.3) |
| Formulation 14 | Etanercept 50 mg/mL, phosphate solution 10 mM, NaCl 120 mM, methionine 12.5 mM (pH 6.3) |
| Control | Etanercept 50 mg/mL, phosphate solution 25 mM, NaCl 100 mM, sucrose 1%, L-arginine 25 mM (pH 6.3) |

After Formulation 13, Formulation 14, and the control were stored at 40° C. for 1 and 3 weeks, and at 25° C. and 4° C. for 4 and 8 weeks each, their Total Impurity was measured by SE-HPLC and HI-HPLC, as in Example 1. The results are shown in Tables 5 and 6, respectively.

TABLE 5

| | Total Impurity by SE-HPLC (%) | | | | | | | | |
|---|---|---|---|---|---|---|---|---|---|
| | 40° C. | | | 25° C. | | | 4° C. | | |
| | 0 week | 1 week | 3 weeks | 0 week | 4 weeks | 8 weeks | 0 week | 4 weeks | 8 weeks |
| Formulation 13 | 5.5 | 11.5 | 20.5 | 5.5 | 14.8 | 18.8 | 5.5 | 8.8 | 10.2 |
| Formulation 14 | 5.5 | 12.5 | 22.0 | 5.5 | 16.0 | 19.9 | 5.5 | 8.9 | 10.5 |
| Control | 5.5 | 13.4 | 23.3 | 5.5 | 16.2 | 20.4 | 5.5 | 8.8 | 10.3 |

TABLE 6

| | Total Impurity by HI-HPLC (%) | | | | | | | | |
|---|---|---|---|---|---|---|---|---|---|
| | 40° C. | | | 25° C. | | | 4° C. | | |
| | 0 week | 1 week | 3 weeks | 0 week | 4 weeks | 8 weeks | 0 week | 4 weeks | 8 weeks |
| Formulation 13 | 10.0 | 15.9 | 21.6 | 10.0 | 15.3 | 18.5 | 10.0 | 11.0 | 11.9 |
| Formulation 14 | 9.9 | 17.0 | 23.3 | 9.9 | 16.7 | 19.8 | 9.9 | 11.3 | 11.6 |
| Control | 10.2 | 18.0 | 25.5 | 10.2 | 17.4 | 20.6 | 10.2 | 10.0 | 11.9 |

As shown in the results of Tables 5 and 6, Formulation 13 and Formulation 14 containing methionine as the stabilizer showed low impurity production under all of the storage conditions of 40° C., 25° C. and 4° C., compared to the control group prepared according to the preparation method of a commercially available etanercept aqueous formulation. Specifically, the SE-HPLC and HI-HPLC results showed that Formulation 13 containing 25 mM methionine and Formulation 14 containing 12.5 mM methionine showed lower impurity production at 40° C. and 3 weeks, and at 25° C. and 8 weeks, and similar impurity production at 4° C. and 8 weeks, compared to the control. These results indicate that the methionine-containing formulation of the present invention is a more stable formulation for maintaining the etanercept activity for a long period of time than the commercially available formulation.

In conclusion, the present invention demonstrated that the etanercept aqueous formulation containing methionine prevents denaturation of etanercept to maintain its activity for a long period of time, and methionine is very effective as a stabilizer in the etanercept aqueous formulation.

Example 3

Stability Test of Etanercept Aqueous Formulation Comprising Histidine and Lysine, or Histidine and Methionine Histidine 5 mM and lysine 25 mM as a stabilizer were added to a 10 mM phosphate solution to which etanercept was added to a concentration of 50 mg/mL, and sodium chloride was added thereto as an isotonic agent to prepare Formulation 15.

In addition, Histidine 5 mM and methionine 25 mM as a stabilizer were added to a 10 mM phosphate solution to which etanercept was added to a concentration of 50 mg/mL, and sodium chloride was added thereto as an isotonic agentto prepare Formulation 16.

Finally, sodium chloride as the isotonic agent was added to a 10 mM phosphate solution and etanercept was added thereto to a concentration of 50 mg/mL to prepare a stabilizer-free formulation.

Each 0.5 mL of the prepared formulation was put in 1.0 mL glass syringes, sealed, and stored at 50° C.

The stabilizer compositions of the formulations are shown in the following Table 7.

TABLE 7

| | Stabilizer composition |
|---|---|
| Formulation 15 | Histidine 5 mM + Lysine 25 mM |
| Formulation 16 | Histidine 5 mM + Methionine 25 mM |
| stabilizer-free formulation | — |

At 7 days after storage at 50° C., Formulations 15, 16 and stabilizer-free formulation of Table 7 were analyzed by SE-HPLC as example 1 to measure their Total Impurity. The results are shown in Tables 8.

TABLE 8

|  | SE-HPLC Total Impurity (%) | |
| --- | --- | --- |
|  | 0 day | 7 days |
| Formulation 15 | 4.7 | 21.5 |
| Formulation 16 | 4.7 | 20.9 |
| stabilizer-free formulation | 4.7 | 30.2 |

As shown in the SE-HPLC results of Table 8, when stored at 50° C. for 7 days, Formulation 16 containing histidine as a stabilizer showed total impurity of 21.5%, and showed remarkably low Total Impurity, compared to the stabilizer-free formulation showing Total Impurity of 30.2%. And Formulation 16 showed remarkably low Total Impurity, compared to Formulation 1 containing 10 mM histidine showing Total Impurity of 22.2%, and Formulation 2 containing lysine 25 mM showing Total Impurity of 24.8%.

That is, the present invention demonstrated that the formulation comprising histidine and lysine has the remarkably excellent effects of preventing etanercept denaturation by reducing the amount of total impurity for storage, compared to the stabilizer-free formulation and each formulation comprising histidine, lysine, and methionine respectively.

In addition, as shown in the SE-HPLC results of Table 8, when stored at 50° C. for 7 days, Formulation 16 containing histidine as a stabilizer showed Total Impurity of 20.9%, which is remarkably low, compared to the stabilizer-free formulation showing Total Impurity of 30.2%. In particular, Formulation 16 showed low Total Impurity compared to Formulation 15 containing histidine and lysine as a stabilizer.

That is, the present invention demonstrated that the formulation comprising histidine and methionine has remarkably effects on the preventing of etanercept denaturation by reducing the amount of Total Impurity for storage, compared to the stabilizer-free formulation.

Example 4

Stability Test of Etanercept Aqueous Formulation Comprising Methionine and Lysine Methionine 12.5 mM and lysine 12.5 mM as a stabilizer were added to a 10 mM phosphate solution to which etanercept was added to a concentration of 50 mg/mL, and sodium chloride was added thereto as an isotonic agent to prepare Formulation 17.

In addition, sodium chloride as the isotonic agent was added to a 10 mM phosphate solution and etanercept was added thereto to a concentration of 50 mg/mL to prepare a stabilizer-free formulation.

Each 0.5 mL of the prepared formulation was put in 1.0 mL glass syringes, sealed, and stored at 50° C. The stabilizer compositions of the formulations are shown in the following Table 9.

TABLE 9

|  | Stabilizer composition |
| --- | --- |
| Formulation 17 | Methionine 12.5 mM + Lysine 12.5 mM |
| stabilizer-free formulation | — |

At 7 days after storage at 50° C., Formulations 17, and stabilizer-free formulation of Table 9 were analyzed by SE-HPLC as example 1 to measure their Total Impurity. The results are shown in Table 10.

TABLE 10

|  | SE-HPLC Total Impurity (%) | |
| --- | --- | --- |
|  | 0 day | 7 days |
| Formulation 17 | 5.2 | 27.0 |
| stabilizer-free formulation | 5.2 | 32.8 |

As shown in the SE-HPLC results of Table 10, when stored at 50° C. for 7 days, Formulation 17 containing methionine and lysine as a stabilizer showed Total Impurity of 27%, which is remarkably low, compared to the stabilizer-free formulation showing Total Impurity of 32.8%.

That is, the present invention demonstrated that the formulation comprising methionine and lysine has remarkably effects on the stabilizing of etanercept by reducing the amount of Total Impurity, compared to the stabilizer-free formulation.

What is claimed is:

1. A liquid formulation of etanercept, consisting of 1 to 100 mg/mL of etanercept, 0.1 to 250 mM of methionine or pharmaceutically acceptable salts thereof as a stabilizer, 0.1 to 100 mM of phosphate buffer, and 1 to 1000 mM of sodium chloride;
   wherein the liquid formulation has an increased storage stability of etanercept compared to the formulation comprising arginine as a stabilizer, by reducing etanercept by products that are produced due to denaturation during storage.

2. A liquid formulation of etanercept, consisting of 1 to 100 mg/mL of etanercept, 0.1 to 250 mM of histidine or pharmaceutically acceptable salts thereof and 0.1 to 250 mM of methionine or pharmaceutically acceptable salts thereof as stabilizers, 0.1 to 100 mM of phosphate buffer, and 1 to 1000 mM of sodium chloride;
   wherein the liquid formulation has an increased storage stability of etanercept compared to the formulation comprising arginine as a stabilizer, by reducing etanercept by products that are produced due to denaturation during storage.

3. A liquid formulation of etanercept, consisting of 1 to 100 mg/mL of etanercept, 0.1 to 250 mM of methionine or pharmaceutically acceptable salts thereof and 0.1 to 250 mM of lysine or pharmaceutically acceptable salts thereof as stabilizers, 0.1 to 100 mM of phosphate buffer, and 1 to 1000 mM of sodium chloride;
   wherein the liquid formulation has an increased storage stability of etanercept compared to the formulation comprising arginine as a stabilizer, by reducing etanercept by products that are produced due to denaturation during storage.

* * * * *